United States Patent [19]
Hollis

[11] Patent Number: 5,821,020
[45] Date of Patent: Oct. 13, 1998

[54] VITAMIN D ASSAY

[75] Inventor: Bruce Warren Hollis, Charleston, S.C.

[73] Assignee: NHH Biologics, East Amherst, N.Y.

[21] Appl. No.: 503,068

[22] Filed: Jul. 14, 1995

[51] Int. Cl.$^6$ ................................................... G01N 33/48
[52] U.S. Cl. ............................ 436/63; 436/161; 436/177
[58] Field of Search ...................... 436/63, 161, 177–178

[56] References Cited

PUBLICATIONS

BIOSIS 91:11549; A Rapid Assay For 25 Hydroxyvitamin D And 1, 25 Dihydroxyvitamin D 24–Hydroxylase, Anal Biochem 190(1). 1990. Abstract Biosis.

Brumbaugh et al., "Filter Assay for 1α,25–Dihydroxyvitamin $D_3$–Utilization of the Hormone's Target Tissue Chromatin Receptor," Biochemistry 13(20):4091–4097 (1974).

Coldwell et al., "Gas Chromatography–Mass Spectrometry and the Measurement of Vitamin D Metabolites in Human Serum or Plasma," Steroids 49(1–3):156–196 (1987).

*Primary Examiner*—Lyle A. Alexander
*Attorney, Agent, or Firm*—Popovich & Wiles, P.A.

[57] ABSTRACT

The present invention provides a method of assaying a sample of blood or blood components, in particular serum, for the presence of 1,25-dihydroxy-vitamin D comprising removing proteins from the sample, incubating the protein-free sample with a salt of periodic acid, isolating 1,25-dihydroxy-vitamin D from the periodate-treated sample, and determining the concentration of 1,25-dihydroxy-vitamin D.

11 Claims, 1 Drawing Sheet

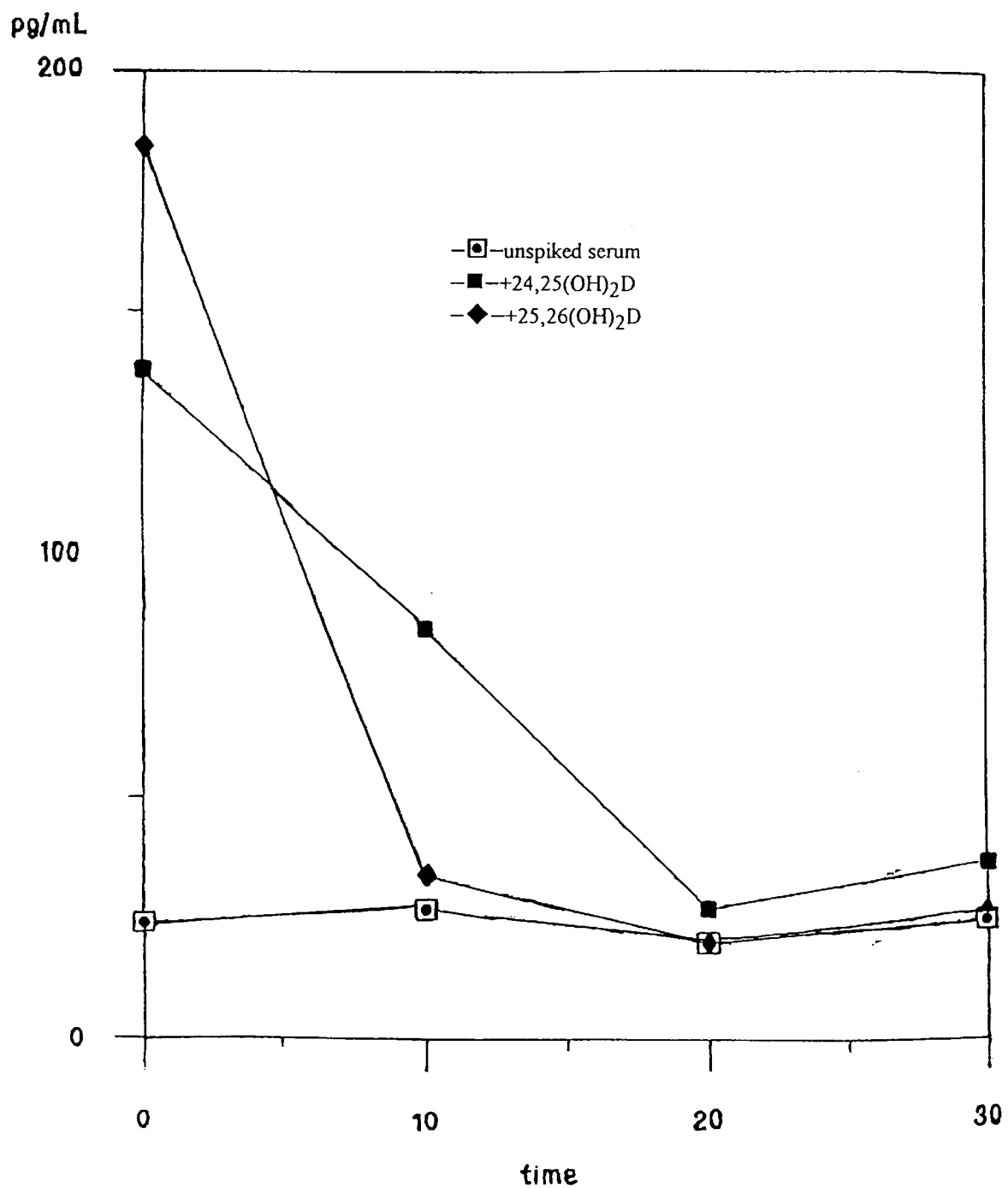

VITAMIN D ASSAY

TECHNICAL FIELD OF THE INVENTION

The present invention relates to a method of assaying a biological sample for the presence of a steroid hormone. In particular, the present invention relates to a method of assaying blood or blood components, in particular serum, for the presence of 1,25-dihydroxy-vitamin D.

BACKGROUND OF THE INVENTION

Vitamin D was discovered as a consequence of the human deficiency disease rickets. Vitamin D is not widely distributed among dietary substances; rather, it is produced in skin. It then undergoes 25-hydroxylation in the liver followed by 1-hydroxylation in the kidney to give the final hormonal form 1,25-dihydroxy-vitamin D (1,25(OH)$_2$D). The production of 1,25(OH)$_2$D is regulated by the need for calcium and phosphorus. A low level of calcium in serum stimulates the parathyroid gland to secrete parathyroid hormone, which, in turn, triggers the production of 1,25(OH)$_2$D in the kidney. The 1,25-dihydroxy derivative then stimulates intestinal absorption of calcium and phosphorus, bone mobilization of calcium, and renal reabsorption of calcium, thereby raising the amount of calcium in the blood to normal levels and, in turn, shutting down parathyroid hormone secretion and the further production of 1,25(OH)$_2$D.

Measurement of the level of 1,25(OH)$_2$D in blood is, therefore, important for the diagnosis of certain diseases, such as kidney failure and osteoporosis, and in the further research into and understanding of these diseases and other conditions related to vitamin D metabolism.

In the past, blood levels of 25-hydroxy-D (25OHD) have been measured by high performance liquid chromatography (HPLC) and by competitive protein binding assays (Eisman et al., Anal. Biochem. 80: 298–305 (1977); and Haddad et al., J. Clin. Endocr. 33: 992–995 (1971)). For example, the vitamin D transport protein known as DBP, which has a strong preference for binding 25 OHD over 1,25(OH)$_2$D or vitamin D, itself, was used in the competitive binding assay (Bouillion et al., J. Steroid Biochem. 13: 1029–1034 (1980)).

Competitive binding assays and antibodies that recognize vitamin D metabolites, e.g., dihydroxycholecaliciferol, have been used to assay for the presence of 1,25(OH)$_2$D (Shigeharu et al., Anal. Biochem. 116: 211–222 (1981); Eisman et al., Arch. Biochem. Biophys. 176: 235–243 (1976); Perry et al., Biochem. Biophys. Res. Comm. 112: 431–436 (1983); Bouillion et al., Ann. Endocrin. 41: 435–436 (1980); Bouillion, Clin. Chem. 26: 562–567 (1980); Bouillion, Eur. J. Biochem. 66: 285–291 (1976)). In such assays, vitamin D and its metabolites were extracted from blood serum or plasma with an organic solvent. The extract was then purified by column chromatography and HPLC to yield 1,25(OH)$_2$D. The isolated 1,25(OH)$_2$D was then added to a mixture of radiolabeled 1,25(OH)$_2$D and either a receptor protein or an antibody, such that the unlabeled 1,25(OH)$_2$D would compete with the radiolabeled 1,25(OH)$_2$D. The degree to which the binding of the labeled 1,25(OH)$_2$D was reduced by unlabeled 1,25(OH)$_2$D was then used to construct a standard curve to determine the amount of 1,25(OH)$_2$D present in the sample.

The level of bound, labeled 1,25(OH)$_2$D was determined by absorbing the free or unbound labeled 1,25(OH)$_2$D on dextran-coated charcoal (see, e.g., Haddad et al., J. Clin. Endocr. 33: 992–995 (1971)). In order to account for the loss of 1,25(OH)$_2$D in each step of the purification process, a measured amount of radiolabeled 1,25(OH)$_2$D was added to the initial plasma or serum extract to correct for the loss. After final purification but before actual measurement of 1,25(OH)$_2$D by binding assay, the radioactivity that remained in the isolated material was counted to allow computation of a recovery. The recovery was then used in the final calculation to correct for the loss of 1,25(OH)$_2$D during purification.

The above assays suffer from a number of disadvantages, including the amount of time, i.e., several days, needed to complete the assay, level of accuracy, and cost. Receptor binding assays require removal of cross-reacting metabolites and interfering lipids, which entails extensive prepurification of serum extracts by chromatography on numerous successive columns, and a fresh preparation of the receptor protein for each assay (Clemens et al., Clinical Endocrinology 11: 225–234 (1979)).

A comparatively simpler competitive binding assay for 1,25(OH)$_2$D might involve adding to a sample of plasma or serum a receptor protein that is capable of binding to 1,25(OH)$_2$D, labeled 1,25(OH)$_2$D, and antibody capable of binding to the receptor protein. The relative degree of binding of the antibody to the receptor bound to labeled 1,25(OH)$_2$D is then measured. This assay simplifies the extraction of vitamin D and its metabolites from the blood plasma or serum prior to the assay. The usefulness of this assay, however, is limited by the lack of an antibody that is specific for 1,25(OH)$_2$D and does not cross-react with 24,25(OH)$_2$D and 25,26(OH)$_2$D.

In view of the above, the present invention seeks to overcome the disadvantages inherent to the above-described methods of assaying for the presence of 1,25(OH)$_2$D. Accordingly, it is an object of the present invention to provide a method of assaying blood or blood components, in particular serum, for the presence of 1,25(OH)$_2$D that substantially reduces the amount of prepurification required and, accordingly, the amount of time needed to complete the assay. In addition, the method is accurate and less costly to perform. These and other objects and advantages of the present invention will become apparent from the description provided herein.

SUMMARY OF THE INVENTION

The present invention provides a method of assaying blood or blood components, in particular serum, for the presence of 1,25 (OH)$_2$D. The method comprises removing proteins from the sample, incubating the protein-free sample with a salt of periodic acid to oxidatively cleave 24,25(OH)$_2$D and 25,26(OH)$_2$D to 25,26,27-nor-24-oxocalciferol and 26-nor-25-ketocalciferol, respectively, then isolating 1,25 (OH)$_2$D from the sample, and determining the concentration of 1,25(OH)$_2$D. Preferably, the sample is serum. The proteins are preferably removed with acetonitrile followed by centrifugation. The salt of periodic acid is preferably sodium periodate or potassium periodate. The 1,25(OH)$_2$D is preferably isolated from the periodate-treated sample by column chromatography. The column preferably is a solid-phase extraction column containing a bed of silica derivatized with octadecyl moieties. The column is preferably consecutively washed with water, around 70% methanol in water, around 10% methylene chloride in hexane, and around 1% isopropanol in hexane. The 1,25(OH)$_2$D is preferably eluted from the column with around 8% isopropanol in hexane and is then dried with nitrogen gas. The concentration of 1,25(OH)$_2$D is preferably determined by immunoassay or by a receptor binding assay.

BRIEF DESCRIPTION OF THE FIGURE

FIG. 1 is a graph of concentration (pg/ml) versus time (min) of treatment with sodium periodate for unspiked serum and serum spiked with either 24,25(OH)$_2$D or 25,26(OH)$_2$D.

DETAILED DESCRIPTION OF THE INVENTION

The present invention stems from the knowledge that 24,25(OH)$_2$D and 25,26(OH)$_2$D are two major vitamin D metabolites that make assay of 1,25(OH)$_2$D difficult. All three compounds have essentially the same molecular weight and similar polarity and, therefore, are not easily separated. Furthermore, all three compounds are recognized by commercially available polyclonal antibodies. An antibody specific for 1,25(OH)$_2$D but not 24,25(OH)$_2$D or 25,26(OH)$_2$D is currently not available.

The present invention is predicated on the discovery that a salt of periodic acid can be used to nondestructively isolate 1,25(OH)$_2$D from 24,25(OH)$_2$D and 25,26(OH)$_2$D from a crude extract derived from a sample of blood or blood components, such as serum, for assay by immunoassay or receptor binding assay, preferably radioimmunoassay. Accordingly, the present invention meets a long-felt need for a simple, accurate and cost-effective method of assaying blood or blood components, in particular serum, for the presence of 1,25(OH)$_2$D that obviates the need for HPLC and a monoclonal antibody specific for 1,25(OH)$_2$D, significantly reduces the amount of sample prepurification required, and, accordingly, the amount of time needed to complete the assay.

A salt of periodic acid can be used to catalyze oxidative cleavage of vicinal diols. In other words, if a compound contains two hydroxyls on adjacent carbons, the periodate salt will cleave the bond between those carbons, thereby converting both carbons to carbonyls. Given that 24,25(OH)$_2$D and 25,26(OH)$_2$D contain vicinal diols, periodate-catalyzed oxidative cleavage of 24,25(OH)$_2$D and 25,26(OH)$_2$D yields the aldehyde 25,26,27-nor-24-oxocalciferol and the ketone 26-nor-25-ketocalciferol, respectively. By virtue of their reduced polarity, the aldehyde and ketone can be easily separated from 1,25(OH)$_2$D by chromatography.

The present inventive method of assaying 1,25(OH)$_2$D in a sample of blood or blood components comprises removing proteins from a sample of blood or blood components, incubating the sample from which protein has been removed with a salt of periodic acid to oxidatively cleave 24,25(OH)$_2$D and 25,26(OH)$_2$D, isolating 1,25(OH)$_2$D from the sample incubated with a salt of periodic acid, and determining the concentration of 1,25(OH)$_2$D as isolated. The sample is preferably serum.

The proteins can be removed from the sample by any one of a number of suitable methods known to those of ordinary skill in the art. A preferred method comprises removing the proteins with acetonitrile, preferably an equal volume, and vortexing intermittently, preferably for about 10 min at room temperature. For purposes of the acetonitrile treatment, all reagents should be allowed to equilibrate to room temperature and care should be taken to ensure that the reagents do not reach temperatures above 25° C. After treatment with acetonitrile, the samples are centrifuged. The centrifugation is preferably conducted at 2,000 rpm for 10 min at room temperature. The protein pellet that results from centrifugation is then discarded.

The resulting supernatant is then mixed with a salt of periodic acid, preferably by gentle vortexing, and incubated to oxidatively cleave 24,25(OH)$_2$D and 25,26(OH)$_2$D to 25,26,27-nor-24-oxocalciferol and 26-nor-25-ketocalciferol, respectively. It is believed that any salt of periodic acid will catalyze the oxidative cleavage of 24,25(OH)$_2$D and 25,26 (OH)$_2$D. Sodium periodate and potassium periodate are preferred. Sodium periodate is especially preferred.

Conditions of incubation of the supernatant with the salt of periodic acid should be such as to promote the desired oxidative cleavage. The salt of periodic acid should be added to the supernatant in sufficient concentration to effect the desired oxidative cleavage within a reasonable period of time. A concentration from about 2.8 mg/ml to about 50.0 mg/ml, preferably from about 25 mg/ml, should be used. A concentration of around 25 mg/ml is preferred for sodium periodate. The temperature of the incubation should be kept moderate, i.e., no extreme temperature should be used. It is preferred that the incubation be carried out at room temperature. Similarly, the pH of the incubation should be at least about 7.0. The incubation should be sufficiently long to ensure complete oxidative cleavage of 24,25(OH)$_2$D and 25,26(OH)$_2$D to 25,26,27-nor-24-oxocalciferol and 26-nor-25-ketocalciferol, respectively. Preferably, the incubation is carried out from about 10 min to about 30 min.

After the incubation of the supernatant with a salt of periodic acid, the 1,25(OH)$_2$D should then be isolated. The 1,25(OH)$_2$D can be isolated by any one of a number of methods known to those of ordinary skill in the art. It is preferred that the 1,25(OH)$_2$D be isolated from the supernatant by column chromatography. Preferably, the column is a solid-phase extraction column containing a bed of silica derivatized with octadecyl moieties. Only HPLC grade solvents and isopropanol, as opposed to 1-propanol, should be used.

A preferred method involves the use of a C$_{18}$OH column, which is prepared by allowing isopropanol, methanol, and distilled water to flow entirely through the column under vacuum pressure, preferably 10 in or approximately 267 mm Hg. Each solvent should be allowed to flow entirely through the column before the next solvent is added to the column. The vacuum may be turned off between solvent additions to the column, if desired. However, the column should not be allowed to air dry for more than 2 min between solvent additions. Once the column has been prepared or regenerated, the protein-free sample is then applied to the column. The column is then consecutively washed to remove 25OHD, 25,26,27-nor-24-oxocalciferol, 26-nor-25-ketocalciferol, lipids, and other interfering substances. Preferably, the column is washed with water, around 70% methanol in water, around 10% methylene chloride in hexane, and around 1% isopropanol in hexane. Then, the vacuum is turned off, the C$_{18}$OH column is placed inside a silica column, and the two columns are secured to ensure adequate vacuum pressure. The 1,25(OH)$_2$D is then transferred to the silica column, preferably by elution with around 8% isopropanol in hexane. The vacuum is again turned off and the C$_{18}$OH column removed. The 1,25(OH)$_2$D is then eluted from the silica column, preferably with around 20% isopropanol in hexane. After vacuum removal, the eluate is dried, preferably under a stream of nitrogen gas (2–4 psi) in either a 37° C. heat block or water bath. If desired, the eluate can be capped and stored at −20° C. for up to 96 hr.

The concentration of 1,25(OH)$_2$D is then determined by any one of a number of methods involving various formats and signal detection systems known to those of ordinary skill in the art. Such formats include, without limitation, competition assays, sandwich assays, displacement assays; etc., involving solid phases, antibody precipitation; etc.

Such signal detection systems are illustrated by various immunoassays, such as radioimmunoassay, enzyme-linked immunoassay, fluorescence immunoassay, chemiluminescence immunoassay, high-sensitivity light scattering immunoassay, fluorescence polarization immunoassay (see, e.g., J. Clin. Immunoassay 7(1): 64 et seq. (Spring 1984)), and receptor binding assay. Labeled vitamin D analogues are suitable for use as tracers in such methods. Preferred methods include radioimmunoassay and receptor binding assay. Radioimmunoassay is more preferred.

A preferred assay comprises reconstituting the sample, as well as standards and control samples, in 95% ethanol with gentle swirling—not vortexing. As before, all reagents should be allowed to equilibrate to room temperature but not allowed to reach temperatures above 25° C. The reconstituted sample is then contacted with a tracer and a primary antibody, such as a dilute antiserum obtained from a sheep immunized with $1,25(OH)_2$ coupled to an immunogenic protein, mixed well, and allowed to incubate for around 2 hr at room temperature. Then, a secondary antibody, such as well-mixed, donkey anti-sheep antiserum, is added to the sample and incubation is continued for another 20 min. When incubation is complete, the sample is centrifuged, preferably at 1800×g (approx. 3,000 rpm) for 20 min, and the supernatant decanted up to 2 min. The radioactivity bound in the pellet is then counted for 1 min in a γ-counter. The amount of $1,25(OH)_2D$ present in the original extract is then calculated by comparing the radioactive counts bound in the sample with a standard curve generated by assaying calibrators containing known amounts of $1,25(OH)_2D$. Counts bound are inversely proportional to the concentration of $1,25(OH)_2D$.

Reagents useful for immunoassay of the isolated $1,25(OH)_2D$ are also contained in commercially available kits (1,25-Dihydroxy Vitamin D $^{125}$I-RIA kit (INCSTAR Corp., Stillwater, Minn.) and Gamma-B 1,25-Dihydroxy Vitamin D RIA kit (IDS Ltd., Tyne and Wear, UK)). Reagents useful for receptor binding assay of the isolated $1,25(OH)_2D$ are also contained in commercially available kits (1,25-Dihydroxy Vitamin D $^3$H-RRA kit (INCSTAR Corp., Stillwater, Minn.) and 1,25-Dihydroxy Vitamin D Radioassay kit (Nichols Institute Diagnostics, Inc., San Juan Capistrano, Calif.)).

The following examples serve to illustrate the present invention and are not intended to limit its scope.

EXAMPLES

Example 1

This example demonstrates the effect of time of incubation of serum with a given concentration of sodium periodate.

A pool of normal human sera was used as a test matrix. Either $24,25(OH)_2D$ or $25,26(OH)_2D$ (20 ng/ml) was added to the matrix. The resultant matrix represented approximately 10× the normal level of these metabolites in serum and, therefore, simulated "worst case" serum samples.

Aliquots of the above test matrix, either unspiked or spiked with the dihydroxylated vitamin D metabolites, were first protein-extracted by addition of an equal volume of acetonitrile followed by centrifugation to remove the precipitated proteins. An equal volume of an aqueous solution of sodium periodate (25 mg/ml) was then added to the resultant supertants, which contained the vitamin D metabolites. The supernatants were then incubated at room temperature for varying times.

After incubation of the supernatants with the periodate salt, the extracts were applied to a solid-phase extraction column containing a bed of silica derivitized with octadecyl moieties. The columns were then washed with water (2 ml), followed by 70% methanol in water (5 ml), then 10% methylene chloride in hexane (5 ml), and, finally, 1% isopropanol in hexane (5 ml). The washes served to remove 25OHD, 25,26,27-nor-24-oxocalciferol, 26-nor-25-ketocalciferol, lipids, and other interfering substances. The $1,25(OH)_2D$ was then eluted from the column with 5% isopropanol in hexane (5 ml), collected in glass tubes, and dried under a gentle stream of nitrogen gas.

The dried extracts were then reconstituted in a small amount of ethanol and combined with a tracer (50 μl) and diluted antiserum (200 μl). The tracer used was $1,25(OH)_2D$ coupled to a radioactive compound, while the antiserum was from a sheep immunized with $1,25(OH)_2D$ coupled to an immunogenic protein. After a 2 hr incubation, a reagent containing donkey anti-sheep antiserum was added to precipitate the sheep anti-$1,25(OH)_2D$. After centrifuging and decanting the supernatant liquid, the radioactivity bound in the pellet was counted in a γ-counter. The amount of $1,25(OH)_2D$ present in the original extract was calculated by comparing the radioactive counts bound in the sample tubes with a standard curve generated by assaying calibrators containing known amounts of $1,25(OH)_2D$. Counts bound are inversely proportional to the concentration of $1,25(OH)_2D$.

The results are summarized in Table I and shown in FIG. 1, which is a graph of concentration (pg/ml) versus time (min) of treatment with sodium periodate for unspiked serum and serum spiked with either $24,25(OH)_2D$ or $25,26(OH)_2D$ as shown.

TABLE I

| | | Apparent $1,25(OH)_2D$ Concentration | |
| --- | --- | --- | --- |
| Time of periodate treatment (min) | Neat serum (pg/ml) | Serum + $24,25(OH)_2D$ (pg/ml) | Serum + $25,26(OH)_2D$ (pg/ml) |
| 0 | 24 | 138 | 184 |
| 10 | 27 | 85 | 34 |
| 20 | 20 | 27 | 20 |
| 30 | 25 | 37 | 27 |

The results show that $24,25(OH)_2D$ and $25,26(OH)_2D$ were removed in a time-dependent manner.

Example 2

This example demonstrates the effect of the concentration of the periodate salt solution on oxidative cleavage of $24,25(OH)_2D$ and $25,26(OH)_2D$ for a given incubation period.

A pool of normal human sera was used as a test matrix. Either $1,25(OH)_2D$, $24,25(OH)_2D$ or $25,26(OH)_2D$ (10 ng/ml) was added to the matrix. Aliquots (1 ml) of the test matrix were then protein-extracted by addition of an equal volume of acetonitrile, followed by centrifugation. An aqueous solution of a varying concentration of sodium periodate (¼th vol.) was added to the supernatants. The supernatants were then incubated at RT for 30 min. After incubation, the periodate-treated extracts were applied to solid-phase extraction columns containing a bed of silica derivatized with octadecyl moieties. The columns were washed and $1,25(OH)_2D$ was eluted from the columns and dried as described in Example 1.

The dried extracts were then reconstituted in a small amount of 5% isopropanol in hexane and injected onto a Zorbax-Sil (DuPont) HPLC column and the column was eluted using the same solvent at a flow rate of 1 ml/min. Eluting vitamin D metabolites were detected by ultraviolet absorbance at 254 nm, and the area under each peak was calculated. The elution times of 1,25(OH)$_2$D, 24,25(OH)$_2$D and 25,26(OH)$_2$D had been determined previously by injection of pure samples of each onto the same columns.

The relative amounts of each metabolite remaining in the column chromatography extracts was estimated by comparing the area under the peak on the HPLC chromatographs with the area under the peak for 1 ng samples of pure metabolite. The results, which are expressed as percent recovery, are summarized in Table II.

TABLE II

| Amount of Sodium Periodate (mg/ml serum) | Percent recovery of Vitamin D metabolites | | |
|---|---|---|---|
| | 24,25(OH)$_2$D | 25,26(OH)$_2$D | 1,25(OH)$_2$D |
| 0 | 1.3% | 15.0% | 55.0% |
| 0.14 | 1.2% | 15.0% | 50.0% |
| 0.7 | 0.4% | 1.5% | 48.0% |
| 2.5 | 0.0% | 0.0% | 51.0% |
| 4.2 | 0.0% | 0.0% | 50.0% |

The results show that the relative amounts of 24,25(OH)$_2$D and 25,26(OH)$_2$D remaining after periodate treatment and column chromatography decreased as the concentration of sodium periodate was increased. The treatment did not appear to adversely affect the recovery of 1,25(OH)$_2$D in any way.

Example 3

This example demonstrates the sensitivity and accuracy of the present inventive method.

Samples of patient serum or serum-based calibrators (500 μl) were extracted with acetonitrile and subjected to rapid chromatography on C18OH-silica solid-phase extraction columns. After drying under nitrogen, the extracts were reconstituted in a small volume of ethanol and duplicate aliquots were combined with an iodinated ($^{125}$I) tracer and sheep anti-1,25(OH)$_2$D. After a 2 hr incubation, a precipitating antibody reagent was added and the tubes were centrifuged to separate bound antibody from free antibody.

The sensitivity of the procedure was determined to be 2 pg/ml. At 20 pg/ml, intra-extract coefficients of variation (CVs) averaged 5.9% and inter-extract CVs averaged 18%. The assay detected both 1,25(OH)$_2$D2 and 1,25(OH)$_2$D3 (100% and 70%, respectively). Crossreactivity with other vitamin D metabolites was minimal. Spike recoveries in normal serum at three different levels ranged from 96–104%.

Using the $^{125}$I-RIA to determine the levels of 1,25(OH)$_2$D in 25 normal subjects, the values ranged from 15.6–59.6 pg/ml (mean=33.1; SD=10.1). Seven pregnant females averages 62.6 pg/ml (SD=25.1) and serum from nine patients with renal failure averaged 13.2 pg/ml (SD=4.8).

Accordingly, these results indicate that the present inventive method is not only simpler, less time-consuming, and more convenient than currently available methods involving the use of receptors and tritium-based tracers, it is sensitive and accurate.

All of the references cited herein, including patents, patent applications and publications, are hereby incorporated in their entireties by reference.

While this invention has been described with an emphasis upon preferred embodiments, it will be obvious to those of ordinary skill in the art that variations in the preferred method can be used, including variations due to improvements in the art, and that it is intended that the invention can be practiced other than as specifically described herein. Accordingly, this invention includes all modifications encompassed within the spirit and scope of the following claims.

What is claimed is:

1. A method of assaying a sample of blood or blood components for the presence of 1,25-dihydroxy-vitamin D comprising:

(a) removing proteins from said sample;

(b) incubating the protein-free sample from step (a) with a salt of periodic acid to oxidatively cleave 24,25(OH)$_2$D and 25,26(OH)$_2$D to 25,26,27-nor-24-oxocalciferol and 26-nor-25-ketocalciferol, respectively;

(c) isolating 1,25(OH)$_2$D from the sample of step (b); and (d) determining the concentration of 1,25(OH)$_2$D isolated in step (c).

2. The method of claim 1 wherein the sample of blood or blood components is serum.

3. The method of claim 1 wherein the proteins are removed from the sample with acetonitrile.

4. The method of claim 1 wherein the salt of periodic acid is selected from the group consisting of sodium periodate and potassium periodate.

5. The method of claim 1 wherein 1,25(OH)$_2$D is isolated by column chromatography.

6. The method of claim 5 wherein the column is a solid-phase extraction column containing a bed of silica derivatized with octadecyl moieties.

7. The method of claim 6 wherein the column is consecutively washed with water, around 70% methanol in water, around 10% methylene chloride in hexane, and around 1% isopropanol in hexane.

8. The method of claim 7 wherein 1,25(OH)$_2$D is eluted from the column with around 8% isopropanol in hexane.

9. The method of claim 8 wherein the eluted 1,25(OH)$_2$D is dried with nitrogen gas.

10. The method of claim 1 wherein the concentration of 1,25(OH)$_2$D is determined by immunoassay.

11. The method of claim 1 wherein the concentration of 1,25(OH)$_2$D is determined by a receptor binding assay.

* * * * *